United States Patent [19]
Litt et al.

[11] Patent Number: 4,508,630
[45] Date of Patent: Apr. 2, 1985

[54] OIL SOLUBLE SULFUR FREE OXYMOLYBDENUM ORGANIC COMPOUNDS HAVING FRICTION REDUCING ANTIWEAR PROPERTIES IN LUBRICANT COMPOSITIONS, PROCESS OF MANUFACTURE, AND LUBRICANT COMPOSITIONS

[75] Inventors: Frederic A. Litt, University Heights; Thomas R. Czernicki, Euclid, both of Ohio

[73] Assignee: The Elco Corporation, Cleveland, Ohio

[21] Appl. No.: 552,860

[22] Filed: Nov. 17, 1983

Related U.S. Application Data

[63] Continuation of Ser. No. 340,498, Jan. 18, 1982, abandoned.

[51] Int. Cl.$^3$ ............ C10M 1/46; C10M 1/54
[52] U.S. Cl. ................ 252/32.5; 260/429 R; 252/49.7; 252/49.8
[58] Field of Search ........... 252/32.5, 32.7 E, 49.7, 252/49.8; 260/429 R

[56] References Cited

U.S. PATENT DOCUMENTS

| | | | |
|---|---|---|---|
| 3,050,538 | 8/1962 | Hugel et al. | 260/429 R |
| 3,402,188 | 9/1968 | Wiese | 252/32.5 |
| 4,289,635 | 9/1981 | Schroeck | 252/32.7 E |

*Primary Examiner*—Jacqueline V. Howard
*Attorney, Agent, or Firm*—Paul & Paul

[57] ABSTRACT

A new class of hydrocarbon-soluble sulfur-free oxymolybdenum compounds is described having the formula

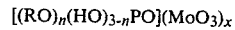

$$[(RO)_n(HO)_{3-n}PO](MoO_3)_x$$

where n=1 to 2; x=more than 1 to 9 except when n=2, then x=not more than 6 and when n=1.5 then x is not more than 7.5. The R radical is defined as substantially hydrocarbyl and may be alkyl, substituted alkyl, aryl, aralkyl, cycloalkyl or alkaryl. The compounds are prepared by the reaction of monoalkyl or dialkyl acid phosphates or mixtures thereof with molybdic oxide suspended in a suitable medium, together with a catalytic amount of a basic material such as an alkali metal hydroxide or hydrosulfide. Lubricant compositions containing these novel compounds are also described.

17 Claims, No Drawings

OIL SOLUBLE SULFUR FREE OXYMOLYBDENUM ORGANIC COMPOUNDS HAVING FRICTION REDUCING ANTIWEAR PROPERTIES IN LUBRICANT COMPOSITIONS, PROCESS OF MANUFACTURE, AND LUBRICANT COMPOSITIONS

This application is a continuation, now abandoned of application Ser. No. 340,498, filed 1/18/82.

This invention relates to novel hydrocarbon-soluble sulfur-free oxymolybdenum compounds having friction reducing antiwear properties in lubricant compositions and to a process for their preparation.

The utility of molybdenum compounds as anti-friction agents was established by the incorporation of molybdenum disulfide, $MoS_2$, into a variety of automotive and industrial lubricants, e.g. oils and greases. Since molybdenum disulfide is insoluble in such oils and greases it must first be stablized as a heterogeneous dispersion to be useful. The stressful conditions under which many of these materials are used often tend to destabilize these dispersions, with subsequent loss of the desirable properties imparted by the molybdenum disulfide. Ensuing filter clogging by coagulated particles can also be a serious problem.

A variety of methods exist for the preparation of oil soluble molybdenum derivatives. These may, in general, be divided into those which produce sulfur-containing molybdenum products (i.e. those where sulfur and molybdenum are both present in the same molecule) and those which produce sulfur-free molybdenum products. The former are represented by disclosures of U.S. Pat. Nos. 2,938,869; 3,010,902; 3,184,410; 3,356,702; 3,400,140; 3,402,188, 3,733,345; 3,931,242; 4,175,043; 4,202,781; 4,192,757; 4,201,683 and 4,208,292. Typical sulfur-free molybdenum products are to be found in U.S. Pat. Nos. 2,805,997; 4,164,473; 4,176,073 and 4,176,074. Chemically, the sulfur-free products of the prior art differ considerably from the compounds of the present invention. U.S. Pat. No. 2,805,997 covers dimers and trimers derived from molybdenum oxide and monohydric alcohols whereas U.S. Pat. Nos. 4,164,473, 4,176,073 and 4,176,074 claim nitrogenous species derived from molybdenum oxide and various amines.

The metal dihydrocarbyl dithiophosphates, e.g. the zinc diaklyl dithiophosphates, constitute a class of additive known to impart antioxidant and antiwear properties. While they affod excellent oxidation resistance and provide superior antiwear properties, it has heretofore been believed that the same significantly limits their ability to decrease friction between moving surfaces. As a result, compositions containing zinc dialkyl dithiophosphates were not believed to provide the most desirable lubricity and, in turn, it was believed that use of compositions containing the same would lead to significant energy loses in overcoming friction even when antifriction agents are included in the composition.

Many of the most effective oxidation and corrosion inhibitors employed heretofore in lubricating oils contain active sulfur. Such inhibitors have an adverse effect on silver, copper and similar metals which are subject to attack by active sulfur. Since these types of metals are being increasingly employed today in certain important classes of internal combustion engines, as for example, marine and railroad diesel engines, it is necessary to find additives which contain no active sulfur.

SUMMARY OF THE INVENTION

The present invention constitutes a new class of compounds represented by the formula $$[(RO)_n(HO)_{3-n}PO](MoO_3)_x$$

where $n=1$ to 2; $x=1$ to 9 except when $n=2$, then $x=$not more than 6 and when $n=1.5$ then x is not more than 7.5. The R radical is defined as substantially hydrocarbyl and may be alkyl, substituted alkyl, al, aryl, aralkyl, cycloalkyl or alkaryl. In addition the hydrocarbyl group may contain a variety of polar substituents, and may also contain nonreactive linkages such as ether oxygens which nevertheless may have an important influence on the properties of the final products.

These pure compounds are useful by incorporation into lubricant compositions either alone or in combination with other compatible lubricant additives.

The novel compounds of this invention may be prepared by reacting monoalkyl or dialkyl acid phosphates or mixtures thereof with molybdic oxide suspended in a suitable medium, together with a catalytic amount of a basic material such as an alkali metal hydroxide or hydrosulfide. Such basic material may be present in an amount from about 0.1–15% molar amounts, while the preferred concentration is an amount from about 5–10% molar amounts. Suitably, the reaction is conducted at a temperature within the range of from about 50° to 150° C. and preferably at a temperature within the range of from about 70° to 90° C., normally for a time period from about 4–36 hours. Preferably the reaction is carried out for a time period from about 12–24 hours at reflux in a suitable reaction medium. Suitable reaction media are alcohols, water, hydrocarbons, ketones, chlorinated solvents and suitable combinations thereof. Preferably simple mixtures of lower alcohols and water are generally used. Any solvent present after the reaction is removed by vacuum stripping, while the product is recovered in its useful form by filtration to give a clear, dark blue, viscous product. Mineral oil is often added to reduce the viscosity.

Mixed monoalkyl and dialkyl phosphates may be prepared in accordance with the following example:

EXAMPLE 1

A three necked flask (2 l.) is equipped with a mechanical stirrer, thermometer and a reflux condenser. 2-Ethylhexanol (1100 g; 8.46 moles) is placed in the flask and phosphorus pentoxide (400 g; 2.82 moles) is added gradually at a rate such that the temperature of the reaction mixture does not exceed 80° C. Total addition requires about 3 hours. Stirring is maintained throughout. External cooling can be applied if necessary or desired. After phosphorous pentoxide addition is complete the batch is stirred for a further 30 minutes and then filtered through a glass fibre filter to remove insoluble impurities. The product is an approximately equimolar mixture of 2-ethylhexyl dihydrogen phosphate(I) and di(2-ethylhexyl) hydrogen phosphate(II) in accordance with the equation.

$$3ROH + P_2O_5 \longrightarrow RO\,P(O)(OH)_2 + (RO)_2\,P(O)(OH).$$
$$\text{I} \qquad\qquad \text{II}$$

where R=2-ethylhexyl.

In its simplest form R is the hydrocarbyl part of an alcohol. The alcohols thus defined are reacted with phosphorus pentoxide to give a mixture of monoalkyl and dialkyl acid phosphates, ROP(O)(HO)$_2$ and (RO)$_2$P(O)OH which in turn react with molybdic oxide (MoO$_3$) suspended in a suitable medium.

The following examples are set forth as representing preferred embodiments of the invention and its utility and are not intended to limit the scope thereof.

EXAMPLE 2

A 2-liter 3-necked flask, equipped with a stirrer, thermometer, condenser and addition funnel, was charged with isopropanol (500 ml.), water (500 ml.) and molybdic oxide (288 g.) The mixture was stirred and heated and sodium sulfhydrate (32 g. of 28% solution, 0.15M) was added, followed by a mixture of 2-ethylhexyl and di-(2-ethylhexyl) phosphates (400 g.) and mineral oil (100 g.) Heating was continued until reflux started and this condition was maintained for 24 hours. The product was stripped to remove solvent and filtered to yield a thick, dark sulfur free blue liquid containing 22.2% Mo and 4.1% P.

EXAMPLE 3

Water (350 g.), isopropanol (2500 g.) and molybdic oxide (2160 g.) were charged to a 12.1 flask equipped with a stirrer, thermometer, condenser and addition funnel. Sodium sulfhydrate (300 g. of 28% solution, 1.5M) was added, followed by a mixture of 2-ethylhexyl and di(2-ethylhexyl) phosphates (4395 g.) and mineral oil (2500 g.) The mixture was stirred and heated to reflux and maintained in that condition for 24 hours. The product was stripped under vacuum, filtered and diluted with mineral oil to give a sulfur free product containing 10.3% Mo and 2.8% P.

EXAMPLE 4

The procedure of Example 2 was followed except that sodium hydroxide (8 g, 0.2M) was used in place of sodium sulfhydrate. The product was obtained as a dark blue sulfur free material containing 26.6% Mo and 3.7% P.

EXAMPLE 5

The procedure of Example 3 was followed except that a mixed phosphate derived from an alcohol mixture was used. The mixture was composed of 60% isodecyl alcohol and 40% n-amyl alcohol (average carbon chain length - C$_8$). The quantities used remain identical in this example. The product, sulfur as isolated, and before the addition of extra mineral oil, had an analysis of 18.3% Mo and 4.8% P.

EXAMPLE 6

The procedure of Example 2 was followed using the acid phosphates of oleyl alcohol (239 g.); molybdic oxide (72 g.); sodium hydrosulfide (8 g. of 28% solution, 0.04M) in 200 ml. of 50/50 isopropanol/water. The product isolated was a dark blue, viscous sulfur free liquid.

EXAMPLE 7

A mixed mono- and dialkyl acid phosphate was prepared from cyclohexanol (300 g.) and phosphorus pentoxide (142 g.). The mixed phosphate (242 g.) was then allowed to react with molybdic oxide (144 g.) in the presence of sodium hydrosulfide (16 g of 28% solution, 0.08M) and 400 ml. of a 50% aqueous isopropanol solution as solvent. The mixture was held at reflux temperature for four hours, then stripped of solvent and filtered. The resulting blue, viscous sulfur free product contained 10.0% Mo and 3.7% P.

EXAMPLE 8

The procedure of Example 6 was followed using a mixed mono- and dialkyl phosphate derived from 2-ethoxyethanol (246 g.). After stripping and filtering a product was obtained which contained 15.0% Mo and 4.1% P.

The utility of molybdenum compounds as lubricant additivies has been illustrated many times. The compounds of this invention are produced by a method which does not result in the inclusion of sulfur. As such the compounds possess friction reducing properties and are able to impart antiwear properties. The compounds are particularly useful for imparting the frictional and antiwear properties of those oils already containing sulfur additives, such as sulfurized sperm oil replacements, dialkyldithio phosphoric acid derivatives, sulfurized hydrocarbons and the like. The incorporation of molybdenum in such a system has the effect of increasing the antiwear and extreme pressure properties of the sulfur-containing fluid.

Lubricant compositions containing effective amounts of the compounds of this invention such as to improve friction reducing and antiwear characteristics of those compositions may readily be prepared. In the following example, the product of Example 5 was incorporated in a lubricant composition as indicated and subjected to standard tests in order to show the utility of the compounds of this invention both with and without an additional sulfur donor.

EXAMPLE 9

| Additive | Wt. % in Oil | % Mo in Oil | Timken OK Load. (lb). ASTM D-2782 | Four-Ball Weld (kg) ASTM D-2783 | EP Test LWI (kg) ASTM D-2783 |
|---|---|---|---|---|---|
| — | — | — | 20 | 160 | 32.3 |
| Ex. 5[1] | 1.0 | 0.08 | 15 | 160 | 40.2 |
| Ex. 5[1] | 5.0 | 0.4 | 30 | 250 | 49.5 |
| Ex. 5[1,2] | 1.0 | 0.08 | 65 | 200 | 41.6 |
| Ex. 5[1,3] | 1.0 | 0.08 | 40 | 200 | 41.6 |

[1] = additive diluted with mineral oil to 8% Mo before use.
[2] = additive as above, but with 1% sulfurized olefin added.
[3] = additive as in 1, but with 1% zinc dialkyldithiophosphate added.

Press-Fit tests (U.S. Steel Lubrication Engineers Manual, p. 118–19) clearly indicate the friction reducing properties of the compounds of this invention on ordinary lubricating oil. The coefficient of friction (u) of 300 SUS Rubrex Oil was determined to be 0.13. The addition of 0.08% Mo in the form of the product of Example 5 reduced the coefficient of friction (u) to 0.09. Increasing the % Mo to 0.24 resulted in a further reduction in the coefficient of friction to 0.06.

Friction reducing properties of the compounds of this invention are further demonstrated in the results obtained with the Falex Model No. 6 in the Four-Ball Wear Test configuration (Faville-LeVally Corp.) Coefficients of friction were measured after 1 minute and after 60 minutes. The average scar diameter of the test balls was also measured. Test conditions were: 20 kg at 1200 rpm, 121° C. Tests were in a fully formulated 10W40 motor oil.

| Additive | Wt. % in oil | % Mo in oil | Coefficient of Friction (1 min) | Coefficient of Friction (60 min) | Av. Scar diameter mm |
|---|---|---|---|---|---|
| None | — | — | 0.045 | 0.064 | 0.39 |
| Ex. 5* | 0.5 | 0.04 | 0.058 | 0.045 | 0.28 |
| Ex. 5* | 1.0 | 0.08 | 0.006 | 0.019 | 0.24 |

*diluted with mineral oil to 8% Mo, 1% sulfurized olefin added.

The above results illustrate both the reduction of friction by the inclusion of small amounts of molybdenum and also increased wear protection as shown by the reduction in scar diameter.

The compounds of this invention were further evaluated is steady state fuel consumption tests. This test is designed to evaluate, under actual operative conditions, the fuel consumption of a vehicle operated under a fixed set of parameters. Data obtained from these tests are shown as Example 10.

EXAMPLE 10

| | Fuel Efficiency: Ford Pinto 2.3 1. Engine | | | | | |
|---|---|---|---|---|---|---|
| | 30 mph | | 45 mph | | 55 mph | |
| | mpg. | % inc. | mpg. | % inc. | mpg | % inc. |
| oil 1 (formulated 10W40) | 26.0 | — | 25.6 | — | 22.7 | — |
| oil 1 + Ex. 5 additive[1] | 26.5 | 1.9 | 25.6 | 0.0 | 23.0 | 1.3 |
| oil 2 (formulated as proprietary | 30.6 | — | 29.4 | — | 26.8 | — |
| oil 2 + Ex. 4 additive[1] | 30.8 | 0.7 | 30.2 | 2.7 | 27.8 | 3.7 |

[1] = Mo content of oil is 0.09%

These results indicate a positive effect (i.e., increased mpg) with those oils containing the additives of this invention.

It will readily be apparent that the novel compounds of this invention may similarly be prepared from either monoalkyl dihydrogen phosphates or dialkyl hydrogen phosphates alone.

Having thus described our invention we claim:

1. Hydrocarbon-soluble sulfur free oxymolybdenum compounds represented by the formula $$[(RO)_n(HO)_{3-n}PO] (MoO_3)_x$$

where n = 1 to 2; x = 1.18 to 9 except when n = 2, then x = not more than 6, and when n = 1.5 then x = not more than 7.5, and R is selected from the group consisting of alkyl, substituted alkyl, aryl, aralkyl, cycloalkyl or alkaryl, including polar substituted embodiments thereof.

2. A composition comprising a major portion of a hydrocarbon and a minor amount of a friction-reducing compound according to claim 1 containing at least about 0.05 percent by weight molybdenum.

3. A lubricating oil composition comprising a major portion of mineral oil and a minor amount of a friction-reducing compound according to claim 1 containing at least about 0.05 percent by weight molybdenum.

4. A compound according to claim 1 wherein the $[(RO)_n(HO)_{3-n}PO]$ moiety comprises a mixture of mono and dialkyl phosphates.

5. The compound according to claim 4 wherein the mixture of mono and dialkyl phosphates is approximately an equimolar mixture of 2-ethylhexyl dihydrogen phosphate and di-(2-ethylhexyl) hydrogen phosphate.

6. A composition in accordance with claim 3 containing additionally a sulfur donor selected from the group consisting of sulfurized olefins, diaklydithiophospate salts and sulfurized sperm oil replacements.

7. A compound according to claim 4 wherein R = a mixture of isodecyl and n-amyl having an average chain length of $C_8$.

8. A compound according to claim 4 wherein R = oleyl.

9. A compound according to claim 4 wherein R = cyclohexyl.

10. A compound according to claim 4 wherein R = 2-ethoxyethyl.

11. A process for producing a hydrocarbon soluble sulfur free oxymolybdenum compound represented by the formula $$[(RO)_n(HO)_{3-n}PO] (MoO_3)_x$$

where n = 1 to 2; x = 1.18 to 9 except when n = 2, then x = not more than 6, and when n = 1.5 then x = not more than 7.5 and R is selected from the group consisting of alkyl, substituted aklyl, aryl, aralkyl, cycloalkyl or alkaryl, including polar substituted embodiments thereof, comprising the steps of reacting a mixture of monoalkyl acid phosphates and dialkyl acid phosphates with molybdic oxide suspended in a suitable medium, in the presence of a catalytic amount of a basic material.

12. The process of claim 11 wherein the basic material is selected from the class consisting of alkali metal hydroxides and hydrosulfides.

13. The process of claim 11 wherein the basic material is present in an amount from about 0.1-15% molar.

14. The process of claim 12 wherein the basic material is present in an amount from about 5-10% molar.

15. The process of claim 11, wherein the reaction is carried out at a temperature within the range of from about 50°-150° C. for a time period from about 4-36 hours.

16. The process of claim 15, wherein the reaction is carried out at a temperature within the range of from about 70° to about 90° C. for a time period from about 12-24 hours.

17. The process of claim 11 wherein the mixture of nomo and dialkyl acid phosphates is approximately an equimolar mixture of 2-ethylhexyl dihydrogen phosphate and di-(2-ethylhexyl) hydrogen phosphate.

* * * * *

UNITED STATES PATENT OFFICE
CERTIFICATE OF CORRECTION

Patent No. 4,508,630                    Dated April 2, 1985

Inventor(s) Frederic A. Litt & Thomas R. Czernicki

It is certified that error appears in the above-identified patent and that said Letters Patent are hereby corrected as shown below:

Column 5, line 33, delete "additive$^{17}$" and insert therefor --additive$^1$--

Signed and Sealed this

Tenth Day of September 1985

[SEAL]

Attest:

DONALD J. QUIGG

Attesting Officer    Acting Commissioner of Patents and Trademarks - Designate